United States Patent
Sonis et al.

(10) Patent No.: US 6,458,777 B1
(45) Date of Patent: Oct. 1, 2002

(54) METHODS AND COMPOSITIONS FOR TREATING AND PREVENTING MUCOSITIS

(75) Inventors: Stephen T. Sonis, Wayland; Edward G. Fey, Boston, both of MA (US)

(73) Assignee: Mucosal Therapeutics LLC, Wellesley, MA (US)

( * ) Notice: Subject to any disclaimer, the term of this patent is extended or adjusted under 35 U.S.C. 154(b) by 0 days.

(21) Appl. No.: 09/265,299

(22) Filed: Mar. 9, 1999

Related U.S. Application Data

(63) Continuation-in-part of application No. 09/065,012, filed on Apr. 23, 1998, now abandoned.
(60) Provisional application No. 60/077,977, filed on Mar. 13, 1998.

(51) Int. Cl.$^7$ ............................................. A61K 31/65
(52) U.S. Cl. .................... 514/152; 514/899; 424/464
(58) Field of Search .................. 514/152, 899; 424/464

(56) References Cited

U.S. PATENT DOCUMENTS

| | | | |
|---|---|---|---|
| 4,666,897 A | | 5/1987 | Golub et al. |
| 5,190,917 A | | 3/1993 | Lezdey et al. |
| 5,192,780 A | | 3/1993 | York et al. |
| 5,215,965 A | | 6/1993 | Lezdey et al. |
| 5,230,895 A | | 7/1993 | Czarnecki et al. |
| 5,310,545 A | | 5/1994 | Eisen |
| 5,385,941 A | | 1/1995 | Fawzi et al. |
| 5,512,055 A | | 4/1996 | Domb et al. |
| 5,578,315 A | | 11/1996 | Chien et al. |
| 5,654,312 A | | 8/1997 | Ardrulis, Jr. et al. |
| 5,674,708 A | | 10/1997 | Cooperman et al. |
| 5,707,653 A | * | 1/1998 | Goldberg .................... 424/464 |
| 5,788,982 A | | 8/1998 | Nadoolman et al. |
| 5,824,297 A | | 10/1998 | Iwata et al. |
| 5,846,525 A | | 12/1998 | Maniar et al. |

FOREIGN PATENT DOCUMENTS

| | | |
|---|---|---|
| EP | 0 355 067 A1 | 2/1990 |
| JP | 7069851 A | 3/1995 |
| JP | 8268854 A | 10/1996 |
| WO | WO 95/17154 A2 | 6/1995 |
| WO | WO 97/09973 A2 | 3/1997 |

OTHER PUBLICATIONS

Physicians Desk Reference, 51st Edition, 1997, p. 2232.*
Amin, et al., "A novel mechanism of action of tetracyclines: effects on nitric oxide synthases," *Proc Natl Acad Sci U S A.* 93(24):14014–9 (1996).
Amon, et al., "CGP 41251, a novel protein kinase inhibitor with in vitro selectivity for protein kinase C, strongly inhibits immunological activation of human skin mast cells and human basophils," *Pharmacology.* 47(3):200–8 (1993).
Armitage, et al., "Microscopic evaluation of clinical measurements of connective tissue attachment levels," *Journal of Clinical Periodontology* 4:173–190 (1977).
Bach, et al., "Experiments on the mode of action of piriprost (U–60,257), an inhibitor of leukotriene formation in cloned mouse mast cells and in rat basophil leukemia cells," *Biochem Pharmacol.* 36(9):1461–6 (1987).
Badger, et al., "Pharmacological profile of SB 203580, a selective inhibitor of cytokine suppressive binding protein/p38 kinase, in animal models of arthritis, bone resorption, endotoxin shock and immune function," *J Pharmacol Exp Ther.* 279(3):1453–61 (1996).
Balla, et al., "Tissue responses to furcation perforations repaired with various dental materials," *Journal of Dental Research* 68:1144 (1989).
Bauditz et al., "Treatment with tumour necrosis factor inhibitor oxpentifylline does not improve corticosteroid dependent chronic active Crohn's disease," *Gut.* 40(4):470–4 (1997).
Bondi, et al., "Local antimicrobial therapy of oral mucositis in Paediatric patients undergoing bone marrow transplant," *Oral Oncology* 33:322–326 (1997).
Caughey, et al., "Bis(5–amidino–2–benzimidazolyl)methane and related amidines are potent, reversible inhibitors of mast cell tryptases," *J Pharmacol Exp Ther.* 264(2):676–82 (1993).
Czarnetzki, et al., "Topical tiacrilast, a potent mast cell degranulation inhibitor, does not improve adult atopic eczema," *Dermatology* 187:112–114 (1993).
De Paulis, et al., "FK–506, a potent inhibitor of the release of proinflammatory mediators from human Fc epsilon Rl+ cells," *J. Immunol.* 146(7):2374–81 (1991).
Fewtrell & Gomperts, "Quercetin: a novel inhibitor of $Ca^{2+}$ influx and exocytosis in rat peritoneal mast cells," *Biochimica et Biophysica Acta* 469:52–60 (1977).
Firali, et al. "Antioxidative activities of some chemotherapeutics. A possible mechanism in reducing gingival inflammation," *J Clin Periodontol* 21(10):680–3 (1994).
Gilbertson–Beadling, et al., "The tetracycline analogs minocycline and doxycycline inhibit angiogenesis in vitro by a non–metalloproteinase–dependent mechanism," *Cancer Chemother Pharmacol.* 36(5):418–24 (1995).
Hallahan, et al., "Ketoconazole attenuates radiation–induction of tumor necrosis factor," *Int J Radiat Oncol Biol Phys.* 29(4):777–80 (1994).

(List continued on next page.)

Primary Examiner—Marianne C. Seidel
Assistant Examiner—C. Delacroix-Muirheid
(74) Attorney, Agent, or Firm—Holland & Knight LLP

(57) ABSTRACT

A method of reducing or inhibiting mucositis in a patient, which includes administering an inflammatory cytokine inhibitor or a mast cell inhibitor, or a combination thereof, is disclosed.

7 Claims, 1 Drawing Sheet

OTHER PUBLICATIONS

Hanazawa, et al., "Expression of Monocyte Chemoattractant Protein 1(MCP–1) in Adult Periodontal Disease: Increased Monocyte Chemotactic Activity in Crevicular Fluids and Induction of MCP–1 Expression in Gingival Tissues," *Infection and Immunity* 61:5219–5224 (1993).

Hanazawa, et al., "Functional Role of Interleukin 1 in Periodontal Disease: Induction of Interleukin 1 Production by *Bacteroides gingivalis* Lipopolysaccharide in Peritoneal Macrophages from C3H/HeN and C3H/HeH Mice," *Infection and Immunity* 50:262–270 (1985).

Hanemaaijer, et al., "Inhibition of MMP synthesis by doxycycline and chemically modified tetracyclines (CMTs) in human endothelial cells," *Adv Dent Res.* 12(2):114–8 (1998).

Hattori, et al., "A metalloproteinase inhibitor prevents lethal acute graft–versus–host disease in mice," *Blood.* 90(2):542–8 (1997).

Hu, et al., "I–FLICE, a novel inhibitor of tumor necrosis factor receptor–1– and CD–95–induced apoptosis," *J Biol Chem.* 272(28):17255–7 (1997).

Jandinski, et al., "Interleukin–Beta in Crevicular Fluids During Periodontal Health and Disease," *Journal of Dental Research Abstracts* 68:1233 (1989).

Jeffcoat, et al., "Treatment of periodontal disease in beagles with lodozamide ethyl, an inhibitor of mast cell release," *Journal of Periodontal Research* 29:532–541 (1985).

Johnson, et al., "The characterization of lodoxamide, a very active inhibitor of mediator release, in animal and human models of asthma," *Agents Actions.* 18(3–4):301–5 (1986).

Kamagata, et al., "Cytokine Production in Human Inflamed Gingival Tissue," *Journal of Dental Reseach Abstracts* 68:525 (1989).

McGeehan, et al., "Regulation of tumour necrosis factor–alpha processing by a metalloproteinase inhibitor," *Nature.* 370(6490):558–61 (1994).

Morimoto, et al., "KB–R7785, a novel matrix metalloproteinase inhibitor, exerts its antidiabetic effect by inhibiting tumor necrosis factor–$\alpha$ production," *Life Sciences* 61:795–803 (1997).

Müllberg, et al., "A metalloproteinase inhibitor blocks shedding of the IL–6 receptor and the p60 TNF receptor," *J Immunol.* 155(11):5198–205 (1995).

Murakami, et al., "Gabexate mesilate, a synthetic protease inhibitor, attenuates endotoxin–induced pulmonary vascular injury by inhibiting tumor necrosis factor production by monocytes," *Crit Care Med.* 24(6):1047–53 (1996).

Pirie–Shepherd, et al., "Differential inhibition of rat mast cell proteinase I and II by members of the $\alpha$–1–proteinase inhibitor family of serine proteinase inhibitors," *The Journal of Biological Chemistry* 266:17314–17319 (1991).

Ranney & Montgomery, "Vascular Leakage Resulting from Topical Application of Endotoxin to the Gingiva of the Beagle Dog," *Archs oral Biol.* 18:963–970 (1973).

Renggli & Regolati, "Intracrevicular sampling of leukocytes using plastic strips," *Helv. Odont. Acta* 16:93–99 (1972).

Siegel, et al., "The measurement of gingival fluid," *J. Periodontol.* 43:682–684 (1972).

Sincholle, et al., "Anti–inflammatory activity of a dual inhibitor of cyclooxygenase and lipoxygenase pathways, CBS–1108 (2–acetylthiophene–2–thiazolylhydrazone)," *Arzneimittelforschung.* 35(8):1260–3 (1985).

Singh, et al., "Capsaicin (8–methyl–N–vanillyl–6–nonenamide) is a potent inhibitor of nuclear transcription factor–kappa B activation by diverse agents," *J Immunol.* 157(10):4412–20 (1996).

Sonis, "Mucositis as a biological process: a new hypothesis for the development of chemotherapy–induced stomatotoxicity," *Oral Oncol.* 34(1):39–43 (1998).

Tilg, et al., "Immune response modulation by pentoxifylline in vitro," *Transplantation* 56:196–201 (1993).

Triplett, et al., "SK&F 86002, a dual cytokine and eicosanoid inhibitor, attenuates endotoxin–induced cardiopulmonary dysfunction in the pig," *Shock.* 6(5):357–64 (1996).

Verdi, et al., "Cancer Therapy and Oral Mucositis," *Drug Safety* 9:185–195 (1993).

Walsh, et al., "Relationship between mast cell degranulation and inflammation in the oral cavity," *J Oral Pathol Med.* 24(6):266–72 (1995).

Greenwald, et al., "Tetracyclines suppress matrix metalloproteinase activity in adjuvant arthritis and in combination with flurbiprofen, ameliorate bone damage," *J. Rheumatol.* 19(6):927–38 (1992).

Pillsbury, et al., "Prostaglandin inhibitor and radiotherapy in advanced head and neck cancers," *Arch Otolaryngol Head Neck Surg.* 112(5):552–3 (1986).

Rothwell & Spektor, "Palliation of radiation–related mucositis," *Spec. Care Dentist.* 10(1):21–5 (1990).

Schenk, et al., "Controlled local delivery of tetracycline HCl in the treatment of periimplant mucosal hyperplasia and mucositis. A controlled case series," *Clin Oral Implants Res.* 8(5):427–33 (1997).

\* cited by examiner

METHODS AND COMPOSITIONS FOR TREATING AND PREVENTING MUCOSITIS

CROSS REFERENCE TO RELATED APPLICATIONS

This application is a continuation-in-part of U.S. Ser. No. 09/065,012, filed Apr. 23, 1998, now abandoned, which claims priority from United States provisional patent application No. 60/077,977, filed Mar. 13, 1998.

BACKGROUND OF THE INVENTION

This invention relates to methods and compositions for treating and preventing mucositis.

Mucositis is the destruction of the oral mucosal epithelium, which results in erythema, ulcerations and severe pain in the oral cavity. Mucositis often arises as a complication of antineoplastic therapy, such as cancer chemotherapy and/or radiation therapy. The painful ulcerative lesions of mucositis can cause patients to restrict their oral intake; as a result, they lose weight and suffer from fever associated with dehydration. Severe mucositis can necessitate the de-escalation of a planned chemo/radio-therapeutic dosing regimen to prevent further damage to the oral mucosa.

An even more serious consequence of mucositis is that the lesions can act as sites of secondary infections and as portals of entry for endogenous oral microorganisms. Mucositis is therefore a significant risk factor for life-threatening systemic infection (septicemia); the risk of systemic infection is exacerbated by concomitant neutropenia, which is another complication associated with chemotherapy. Patients with mucositis and neutropenia have a relative risk of septicemia that is at least four times greater than that of individuals without mucositis.

The overall frequency of mucositis varies; it is influenced by the patient's diagnosis, age, and level of oral health, as well as the type, dose, and frequency of drug or radiation administration. Approximately 40% of all patients who receive cancer chemotherapy suffer some degree of mucositis, and virtually 100% of patients treated with radiation therapy for head and neck tumors develop mucositis. The frequency of severe mucositis in patients undergoing high risk protocols is over 60%. About 50% of individuals develop lesions severe enough to require modification of their cancer treatment and/or parenteral analgesia.

The development of effective methods for treating and preventing mucositis has been hampered by a lack of understanding of the pathophysiology of this condition, and by the inconsistency in patient response to the medications currently in use.

SUMMARY OF THE INVENTION

The invention features methods for treating and preventing mucositis. The invention is based, in part, on the recognition that mucositis is a complex biological process resulting from the cumulative and interactive effects of radiation and/or chemotherapy with epithelial connective tissue and endothelium, pro-inflammatory cytokines, cellular elements within the mucosa and the local oral environment.

We hypothesize that mucositis represents a clinical outcome due to a complex interaction of local tissue (connective tissue, endothelium, epithelium) toxicity, the level of myelosuppression and the oral environment. The local tissue components include an oral mucosa of rapidly renewing stratified squamous epithelium overlying a loose and richly vascular connective tissue base and appear to be responsive to changes in patients' bone marrow status and, particularly, the degree of granulocytopenia. The oral microbial flora, saliva and functional trauma provide an indigenous environment which impacts on the frequency, severity and course of chemotherapy-associated stomatotoxicity.

It is quite likely that the initial oral tissue response to chemotherapy and radiation occurs at the endothelial and connective tissue level. We believe that free radical formation leads to the disruption of fibronectin with subsequent activation of transcription factors, stimulation of pro-inflammatory cytokine production and tissue damage. A relationship between the presence of tumor necrosis factor-alpha (TNF-$\alpha$) and IL-1 in serum correlates with the presence of non-hematologic toxicities. It is also likely that injury to endothelial cells occurs simultaneously. Concurrently, damage to the basal epithelial cells prevents their replication. It is unclear whether many of these cells undergo apoptosis or necrosis. An influx of inflammatory cells expressing pro-inflammatory cytokines occurs during the breakdown of the mucosa and peaks just prior to the acme of mucositis. Bacterial colonization of the damaged epithelium occurs and is accelerated by the patient's myelosuppressed state. Typically the nadir follows a day or so after peak mucositis. Bacterial cell wall products from both gram positive and gram negative organisms likely then penetrate the injured mucosa and further stimulate the release of damaging cytokines. Finally, the mucosa recovers, a process which takes about three weeks in the absence of secondary infection.

According to the invention, mucositis can be treated, or even prevented, by the administration of inflammatory cytokine inhibitors, MMP inhibitors, and/or mast cell inhibitors. The combination of these inhibitors with an anti-inflammatory agent and/or an antimicrobial agent provides an even more effective regime for preventing and treating mucositis.

The invention features a method of reducing or inhibiting mucositis, in a patient suffering from mucositis or at risk for mucositis; the method includes administering to the patient a first therapeutic agent in an amount sufficient to inhibit mucositis, where the first therapeutic agent is an inflammatory cytokine inhibitor, a mast cell inhibitor, an MMP inhibitor, or a combination of these inhibitors. Preferred mast cell inhibitors include degranulation inhibitors, antihistamines, and serine protease inhibitors. A preferred MMP inhibitor is a tetracycline such as minocycline, which used by itself in low doses is an effective mucositis agent that does not primarily act as an antibiotic. Other members of the tetracycline family can be used as well, e.g., chlortetracycline and oxytetracycline. An example of a mucositis that can be reduced or inhibited according to the invention is oral mucositis.

The invention also features a method of treating, inhibiting, or preventing mucositis in the human patient by administering to the patient first and second different therapeutic agents, the first agent being an NSAID (non-steroidal anti-inflammatory), an inflammatory cytokine inhibitor, or a mast cell inhibitor, and the second agent being an inflammatory cytokine inhibitor, a mast cell inhibitor, an MMP inhibitor, an NSAID, or an NO inhibitor. Preferably at least one of the agents is an NSAID, which is a COX-1 or COX-2 inhibitor; examples of COX-1 inhibitors are indomethacin and flurbriprofin. In other preferred embodiments, the first agent is an inflammatory cytokine inhibitor selected from an IL-6 inhibitor, a TNF-alpha inhibitor, an IL-1 inhibitor, and an interferon-gamma inhibitor. A preferred combination is a TNF-alpha inhibitor combined with an MMP inhibitor such as a tetracycline, eg, minocycline. Exemplary NO inhibitors are aminoguanidine and guanidine. Another TNF-alpha inhibitor that can be used is thalidomide. Mast cell inhibitors can be antihistamines, serine protease inhibitors, or degranulation inhibitors.

In other preferred methods, a third therapeutic agent, in an amount sufficient to inhibit infection, is administered as well; the third therapeutic agent includes an antimicrobial compound. Preferably, the first, second, and third therapeutic agents are administered concurrently.

In another preferred method, the first therapeutic agent, in an amount sufficient to inhibit mucositis, and the third therapeutic agent, in an amount sufficient to inhibit infection, are administered. Preferably, the first therapeutic agent and the third therapeutic agent are administered concurrently.

The mucositis being treated can be induced by antineoplastic therapy; for example, it can be induced by chemotherapy or by radiation therapy. The patient treated with the methods and compositions of the invention can be a cancer patient preparing to undergo chemotherapy or radiation therapy, or a cancer patient currently undergoing chemotherapy or radiation therapy.

The invention further features a pharmaceutical composition for treating oral mucositis that includes (a) a first therapeutic agent including an inflammatory cytokine inhibitor, a mast cell inhibitor, an MMP inhibitor or a combination of these inhibitors; (b) a second therapeutic agent including an anti-inflammatory agent; and (c) a pharmaceutically acceptable carrier. The first and second therapeutic agents are present in amounts sufficient to inhibit mucositis in a patient suffering from mucositis or at risk for mucositis. Preferably, the composition is formulated into a lozenge, a tablet, an oral rinse, an oral paste, or an oral gel. A preferred mast cell inhibitor is an antihistamine; preferred anti-inflammatory agents include non-steroidal anti-inflammatory drugs and cyclooxygenase-2 inhibitors. Preferred MMP inhibitors include tetracyclines such as minocycline, tetracycline HCl, or doxycycline. Preferred compositions can also include an anti-ulcer agent, in an amount sufficient to inhibit gastric mucosal injury, and an antimicrobial agent, in an amount sufficient to inhibit infection.

DESCRIPTION OF THE PREFERRED EMBODIMENTS

Figure 1:
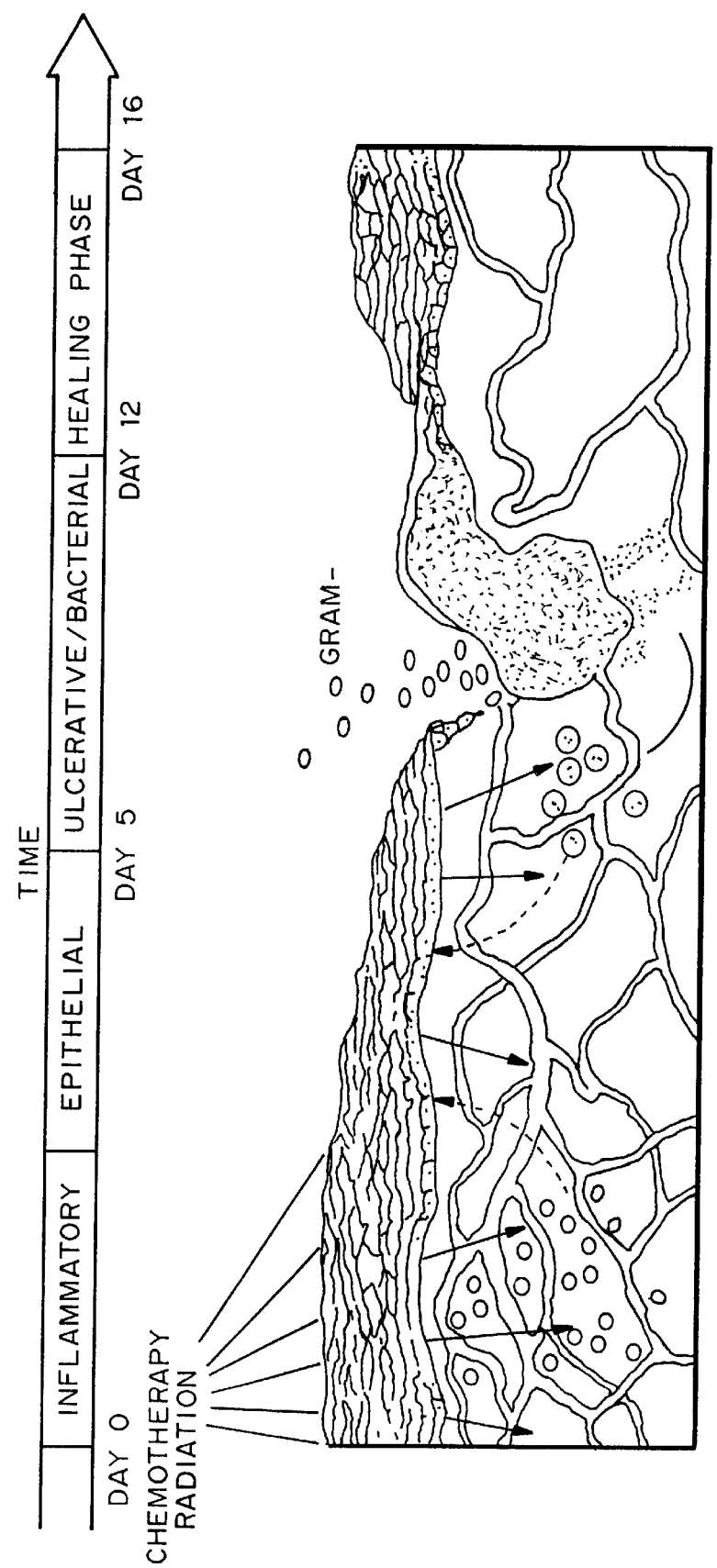
FIG. 1 is a schematic representation illustrating the four phases of mucositis development and resolution.

The invention features methods and compositions for reducing and inhibiting mucositis that include administering inflammatory cytokine inhibitors and/or mast cell inhibitors.

The invention is based, in part, on the development of a new mechanistic scheme for the physiological basis of mucositis. According to this scheme, the development and resolution of mucositis occurs in four interrelated phases: (i) an inflammatory/vascular response; (ii) a degenerative connective tissue and/or epithelial phase; (iii) an ulcerative/bacteriological phase; and (iv) a healing phase. The four phases are illustrated in FIG. 1.

During phase 1, the inflammatory or vascular phase, the administration of chemotherapy effects the release of the cytokines interleukin-1 (IL-1), interleukin-6 (IL-6), and tumour necrosis factor-alpha (TNF-α) from the epithelium. Alternatively, the administration of ionizing radiation causes the release of these cytokines from both the epithelium and from the surrounding connective tissues.

IL-1 induces an inflammatory response that results in increased sub-epithelial vascularity, with a consequent increase in the local levels of cytotoxic agents. Both IL-1 and TNF-α cause local tissue damage, and thereby initiate and accelerate mucositis.

During phase 2, the degenerative epithelial phase, radiation and chemotherapeutic drugs affect the endothelium, the connective tissues and the dividing cells of the oral basal epithelium, resulting in reduced epithelial renewal, atrophy, and ulceration. The ulceration of the surrounding tissue is exacerbated by functional trauma and by a flood of locally produced cytokines.

Phase 3, the ulcerative/bacterial phase, is the most symptomatic and perhaps the most complex. This phase generally occurs at the time of the patient's maximum neutropenia. Phase 3 is characterized by the release of agents that stimulate cytokine production from bacteria on the lesions. Localized areas of full-thickness erosion develop, and a fibrous pseudomembrane sometimes grows over these areas. Secondary bacterial colonization of the lesions occurs, including colonization with both gram positive and negative organisms; this stimulates cytokine release from the surrounding connective tissue, which further amplifies local tissue destruction.

During phase 4, the healing phase, epithelial proliferation and differentiation is renewed, the peripheral white blood cell count is normalized, and the local microbial flora is re-established.

These four phases are interdependent; they are the consequence of a series of actions mediated by cytokines, the direct effect of the antineoplastic agents on the epithelium, connective tissue and endothelium, the oral bacterial flora, and the status of the patient's bone marrow.

The invention is also based, in part, on the discovery that proliferation of mast cells plays a key role in the development of mucositis. Mast cells are granule-containing secretory cells which are present in mucosal and connective tissues, and which can migrate within these tissues. The distribution of mast cells in tissues generally relates to the potential of mast cell-derived mediators to influence cells in the immediate environment. In the oral cavity, mast cells are preferentially distributed within the microvascular bed of the mucosa.

The granules of mast cells contain mediators that promote inflammation. Following degranulation, which can be triggered by a variety of stimuli, such as IgE, neuropeptides, trauma, and drugs, the mast cell mediators are deposited in large quantities in the extracellular environment. These mediators include histamine; the serine proteases chymase and tryptase; and cytokines, including TNF-α. The mediators promote inflammation by exerting their effects on endothelial cells and other cell types. For example, the mediators may influence adhesion molecules and the behavior of the tissue, leading to ulceration.

Two of the most important of these mediators are histamine and TNF-α. In the normal oral mucosa, these mediators are present only in the granules of mast cells, and are absent in other cells.

Mast cell-released histamine increases vascular permeability by effecting structural changes, such as endothelial contraction and intercellular gap formation. These changes result in increased local levels of chemotherapy-induced damage. In addition, histamine promotes leukocyte adhesion to endothelial cells via transient mobilization of the adhesion molecule, P-selectin, thereby causing inflammation.

Another important mediator released by mast cells is the cytokine TNF-α. TNF-α contributes to the inflammatory process by releasing histamine and by inducing endothelial expression of E-selectin, an adhesion molecule which is critically required for the rapid adhesion of neutrophils, T cells, monocytes, and other leukocytes to endothelial cells.

According to the invention, agents that inhibit the function of the mast cells or the action of the mediators released by mast cells can be used to treat and prevent mucositis. Mast cell inhibitors are chemical or biological agents that suppress or inhibit the function of mast cells, or the mediators released by mast cells. For example, mast cell inhibitors can inhibit degranulation, thereby preventing the release of mediators into the extracellular space. Examples of mast cell degranulation inhibitors include picetannol, benzamidines, tenidap, tiacrilast, disodium cromoglycate, lodoxamide ethyl, and lodoxamide tromethamine. Other agents that inhibit mediator release include staurosporine and CGP 41251.

Examples of mast cell mediator inhibitors include agents that block the release or secretion of histamine, such as FK-506 and quercetin; antihistamines such as diphenhydramine; and theophylline.

Other mast cell inhibitors include serine protease inhibitors, such as α-1-protease inhibitor; metalloprotease inhibitors; lisofylline; TNFR-FE (available from Immunex, Seattle, Wash.); benzamidine; amiloride; and bis-amidines such as pentamidine and bis(5-amidino-2-benzimidazolyl) methane.

According to the invention, inflammatory cytokine inhibitors can also be used to treat and prevent mucositis. Inflammatory cytokine inhibitors are chemical or biological agents that suppress or inhibit inflammatory cytokines. Such inhibitors include pyridinyl imidazoles, bicyclic imidazoles, oxpentifylline, thalidomide and gabexate mesilate.

Anti-inflammatory agents can be used in combination with inflammatory cytokine and/or mast cell inhibitors to treat and prevent mucositis according to the invention. Examples of anti-inflammatory agents that can be used in the present invention include the non-steroidal anti-inflammatory drugs flurbiprofen, ibuprofen, sulindac sulfide, and diclofenac. When NSAID's are administered according to the invention, anti-ulcer agents such as ebrotidine can be administered, e.g., to help protect against gastric mucosal damage.

Other anti-inflammatory agents that can be used in the present invention include misoprostil; methylxanthine derivatives, such as caffeine, lisofylline, or pentoxyfylline; benzydamine; naprosin; mediprin; and aspirin.

Another important class of anti-inflammatory agents includes cyclooxygenase (COX) inhibitors, particularly COX-2 inhibitors. COX-2, an inducible enzyme stimulated by growth factors, lipopolysaccharide, and cytokines during inflammation or cell injury, is responsible for the elevated production of prostaglandins during inflammation. COX-2 inhibitors are especially useful where the invention is used to treat mucositis in cancer patients undergoing chemotherapy or radiation therapy, because of the gastrointestinal tolerability of these inhibitors. COX-2 inhibitors that can be used in the invention include celecoxib, nimesulide, meloxicam, piroxicam, flosulide, etodolac, nabumetone, and 1-[(4-methylsulfonyl)phenyl]-3-trifluoromethyl-5-[(4-fluoro)phenyl]pyrazole.

Other useful anti-inflammatory agents include dual cyclooxygenase/lipoxygenase inhibitors, such as 2-acetylthiophene-2-thiazolylhydrazone, and leukotriene formation inhibitors, such as piriprost.

MMP inhibitors include both the antibacterial tetracyclines such as tetracycline HCl, minocycline and doxyocycline, as well as non-antibacterial tetracyclines.

The presence of bacteria in the oral cavity leads to secondary infection, serves as a source for systemic infection, and stimulates cytokine release, thereby amplifying tissue damage. According to the invention, the administration of anti-microbial agents in combination with the agents described above can result in an even more effective method for treating and preventing mucositis. Examples of antimicrobial agents that can be used include agents with spectrum for gram positive and gram negative organisms. Specific drugs include tetracycline, amoxicillin, gentamicin, and chlorhexidine.

Other agents that can be used to treat or prevent mucositis include the nuclear transcription factor kappa-B (NF-κB) activation inhibitors capsaicin and resiniferatoxin.

Route and Timing of Administration

The route of administration is governed by the nature of the compound(s) used. For example, the compounds can be administered in tablet or lozenge form, as an oral rinse, as a paste or gel, or by parenteral administration.

Since the compositions of the invention can help prevent mucositis, administration of the compositions should preferably precede the initial dose of antineoplastic therapy by at least 24 hours. Daily treatment should continue during the course of antineoplastic treatment.

Dosage

The therapeutic agents described above can be used in the dose ranges currently used for these agents. For topical application, the amount of drug to be administered will produce local tissue dose ranges equivalent to, or higher than, those achieved by parenteral administration. The following are illustrative examples of dose ranges.

Mast Cell Function Inhibitors

The mast cell function inhibitor, picetannol, is preferably administered to tissue or plasma levels of 0.1 $\mu$g/ml to 5 $\mu$g/ml; benzamidines are preferably administered to tissue or plasma levels of 0.5 to 1.0 $\mu$M/l; tenidap is preferably administered to tissue or plasma levels of 1–200 $\mu$M/l; and tiacrilast is administered in a 1% to 10% solution.

Mast Cell Mediator Inhibitors

With respect to mediator inhibitors, lisofylline is preferably administered at 1 mg/kg to 10 mg/kg body weight, and TNFR-Fe (Immunex, Seattle, Wash.) is administered in 25 mg doses, twice weekly.

Anti-inflammatory agents

The anti-inflammatory agent, ibuprofen, is preferably administered at 50 mg to 800 mg per day, and flurbiprofen is preferably administered at 50 mg to 300 mg per day. The COX-2 inhibitor etodolac is preferably administered at 500 to 2000 mg per day; nabumetone is preferably administered at 500 to 2000 mg per day; meloxicam is preferably administered at 7.5 to 25 mg per day; piroxicam is preferably administered at 10 to 30 mg per day; and 1-[(4-methylsulfonyl)phenyl]3-trifluoromethyl-5-[(4-fluoro)phenyl]pyrazole is preferably administered at 1 to 10 mg/kg per day.

Anti-microbial Agents

With respect to anti-microbial agents, tetracycline is preferably administered at 250 mg to 1000 mg per day, and chlorhexidine is preferably administered in a 0.1 to 5% solution, twice daily.

Without further elaboration, it is believed that one skilled in the art can, based on the description herein, utilize the present invention to its fullest extent. The following specific examples are, therefore, to be construed as illustrative of the invention, and are not meant to limit the remainder of the disclosure in any way. Publications mentioned herein are hereby incorporated by reference.

MMP Inhibitors

Tetracyclines used as MMP inhibitors will be administered topically in dosages of 0.001 to 10 mg/mL, with a probable range of 0.01 to 1 mg/mL, and an optimal range of 0.05 to 0.5 mg/mL.

EXAMPLE 1

Prophylaxis and Treatment for Patients Undergoing Myeloablative Chemotherapy and Total Body Irradiation in Preparation for Bone Marrow Transplantation For treatment according to the methods described herein, patients are dosed with a topical application of mucositis medication as a troche or lozenge, beginning the evening before the first dose of chemotherapy. The lozenge contains therapeutic doses of an MMP inhibitor such as minocycline and a nonsteroidal anti-inflammatory agent such as flurbiprofen.

Beginning the day of chemotherapy and continuing for the subsequent fourteen days, patients receive medication every 3 to 4 hours while awake. For patients unable to tolerate the lozenge because of chemotherapy-induced nausea, a non-viscous liquid suspension is available for dosing approximate every 2 hours while awake. Patients using the suspension swish and gargle with the material to assure exposure of the drug to the oropharynx. The fourteen-day dosing period provides coverage through the first three phases of mucositis development.

EXAMPLE 2

Prophylaxis and Treatment for Patients Undergoing Radiation Therapy for Tumors of the Head and Neck Patients being treated with radiation therapy for head and neck cancers receive a total tumor dose of radiation of about 60 Gy, given in divided doses over a 6-week to 8-week period. Early signs of mucositis are noted at doses of around 10 Gy, and frank breakdown of the mucosa is seen at around 25 Gy.

Beginning with the second week of this type of radiation therapy, patients receive mucositis medication 2 hours prior to each daily dose of radiation, which is typically given 5 days per week. Subsequent mucositis medication is given 2 hours, 6 hours, and 12 hours following daily radiation. Since myelosuppression is not an issue for patients being radiated for head and neck cancers, the mucositis preparation includes mast cell inhibitors, cytokine inhibitors, and anti-inflammatory agents, but no anti-microbial agents. Patients do not receive mucositis medication on days on which they are not radiated. The protocol is followed until radiation dosing is completed.

EXAMPLE 3

Prophylaxis and Treatment for Patients Undergoing Chemotherapy Treatment for Treatment of Colorectal Cancer In treatments for colorectal cancer, patients typically receive multiple, monthly cycles of chemotherapy. Because of the use of specific anti-cancer drugs for treatment of this form of tumor, this group of patients is at particular risk for developing mucositis. Patients in this group begin dosing with mucositis medication two hours prior to chemotherapy administration. They continue taking mucositis medication every 4 hours, while awake, for at least the next 48 hours. The regimen is repeated for each dosing cycle. Generally, the formulation does not include an anti-microbial. However, for those patients demonstrating significant neutropenia, the formulation includes an anti-microbial, and treatment time is extended to ten days.

Other Uses

The methods and compositions of the present invention can be used to treat and prevent conditions such as lichen planus and graft-vs-host disease, which have similar biological mechanisms to that of mucositis.

Other embodiments are within the scope of the following claims.

What is claimed is:

1. A method of treating a patient undergoing radiation treatment or chemotherapy to prevent or reduce the severity of mucositis comprising administering to the patient a formulation comprising an active agent, wherein the active agent consists essentially of an effective amount of a tetracycline to decrease duration or severity of mucositis when applied to the mucosal surface.

2. The method of claim 1 wherein the tetracycline is in a concentration of between 0.01 and 1 mg/ml.

3. The method of claim 2 wherein the tetracycline is in a concentration of between 0.1 and 1.0 mg/ml.

4. The method of claim 1 wherein the formulation is selected from the group consisting of a oral rinse, tablet, lozenge, paste and gel.

5. The method of claim 1 wherein the formulation is administered to the patient one day before the patient is treated with chemotherapy or radiation.

6. The method of claim 1 wherein the formulation is administered at least daily to a patient undergoing radiation or chemotherapy.

7. The method of claim 1 wherein the patient is a cancer patient.

* * * * *

Disclaimer

6,458,777 — Stephen T. Sonis, Wayland; and Edward G. Fey, Boston, both of MA (US). METHODS AND COMPOSITIONS FOR TREATING AND PREVENTING MUCOSITIS. Patent dated October 1, 2002. Disclaimer filed November 8, 2012, by the assignee, Mucosal Therapeutics LLC.

Hereby enters this disclaimer to claims 1-7 of said patent.

*(Official Gazette, December 18, 2012)*